United States Patent [19]

Yokomori et al.

[11] Patent Number: 5,304,476

[45] Date of Patent: Apr. 19, 1994

[54] PROCESS FOR PRODUCING L-LYSINE BY FERMENTATION EMPLOYING A MICROORGANISM RESISTANT TO ACYL-LYSINE OR METHYLATED ACYL-LYSINE

[75] Inventors: Manabu Yokomori; Kazuhiko Totsuka; Yoshio Kawahara; Harufumi Miwa, all of Kawasaki; Tsuyoshi Osumi, Tokyo, all of Japan

[73] Assignee: Ajinomoto Co., Inc., Tokyo, Japan

[21] Appl. No.: 845,139

[22] Filed: Mar. 3, 1992

[30] Foreign Application Priority Data

Mar. 6, 1991 [JP] Japan ................... 3-123285

[51] Int. Cl.$^5$ ................ C12P 13/08; C12N 01/20
[52] U.S. Cl. ................ 435/115; 435/252.1; 435/843; 435/840
[58] Field of Search ........ 435/106, 115, 252.1, 435/172.1, 840, 843

[56] References Cited

U.S. PATENT DOCUMENTS

| | | | |
|---|---|---|---|
| 3,708,395 | 1/1973 | Nakayama et al. | 435/115 |
| 3,732,144 | 5/1973 | Nakayama et al. | 435/115 |
| 3,905,867 | 9/1975 | Kurimura et al. | 435/115 |
| 4,066,501 | 1/1978 | Tosaka et al. | 435/115 |

FOREIGN PATENT DOCUMENTS 2341647  9/1977  France.

OTHER PUBLICATIONS

Hirao et al., "L-lysine Production in Continuous Culture ... glutamioum", Appl. Microbiol Biotechnol vol. 32, pp. 269-273, 1989.

Tosaka et al., "Lysine", In: Biotechnology of Amino Acid Production, vol. 24; Elsevier; Aida et al. (eds.); pp. 152-172; 1986.

Primary Examiner—Marian Knode
Attorney, Agent, or Firm—Oblon, Spivak, McClelland, Maier & Neustadt

[57] ABSTRACT

The present invention relates to a fermentation process using a L-lysine-producing microorganism having a resistance to an acyl-lysine, a methylated acyl-lysine or both an acyl-lysine and a methylated acyl-lysine. By the process of the present invention, L-lysine may be produced in high yields providing an improved process that reduces the cost of industrially produced L-lysine.

4 Claims, No Drawings

PROCESS FOR PRODUCING L-LYSINE BY FERMENTATION EMPLOYING A MICROORGANISM RESISTANT TO ACYL-LYSINE OR METHYLATED ACYL-LYSINE

BACKGROUND OF THE INVENTION

1. Field of the Invention

L-lysine is an important amino acid used as a feed additive for broilers and swine, as examples, because the amount of L-lysine is insufficient in feed crops such as corn. The present invention relates to a improved process for producing L-lysine by fermentation.

2. Discussion of the Background

Previous known conventional methods for producing L-lysine by fermentation comprise imparting properties necessary for acquiring the L-lysine productivity such as homoserrne auxotrophy, S-(2-aminoethyl)-L-cysteine resistance, α-chlorocaprolactam resistance, for example, to microorganisms belonging to the genus Brevibacterium or the genus Corynebacterium which were isolated from nature (hereafter referred to as wild strains), culturing the microorganisms in a medium containing carbon sources and nitrogen sources, for example, and collecting the L-lysine produced and accumulated in the culture broth by resin adsorption, for example.

Furthermore, a process using improved strains of these L-lysine-producing microorganisms, for example, L-alanine auxotrophs, fluoropyruvate sensitive strains, and L-leucine analog resistant strains, has also been studied but the yield of L-lysine produced by fermentation is not yet satisfactory. Thus, the need exists for the development of a more efficient process for producing L-lysine at lower costs than those previously provided by the conventional processes.

The present invention provides for such a process that efficiently produces L-lysine at lower costs than the previously known processes by enhancing the L-lysine productivity of L-lysine-producing microorganisms or mutants thereof, thereby improving the fermentation yield.

SUMMARY OF THE INVENTION

It is an object of the present invention to provide a process for producing L-lysine by fermentation in greater yields than previously described comprising culturing a microorganism having a resistance to acyl-lysine, methylated acyl-lysine or resistance to both acyl-lysine and methylated acyl-lysine and capable of producing L-lysine and collecting L-lysine from the culture broth.

In another embodiment, the present invention relates to the process described above wherein the microorganism is obtained from the genus Brevibacterium, the genus Corynebacterium or mutants thereof.

In a further embodiment, the present invention relates to a mutant strain microorganism derived from the genus consisting of Brevibacterium and Corynebacterium having a resistance to an acyl-lysine, a methylated acyl-lysine or resistance to both an acyl-lysine and a methylated acyl-lysine.

In another embodiment, the present invention relates to the microorganism *Brevibacterium lactofermentum* AJ 12592, (FERM BP-3239) having a resistance to an acyl-lysine.

In another embodiment, the present invention relates to the microorganism, *Brevibacterium lactofermentum* AJ 12593 (FERM BP-3240) having a resistance to a methylated acyl-lysine.

In still another embodiment, the present invention relates to the microorganism, *Corynebacterium glutamicum* AJ 12596 (FERM BP-3242) having a resistance to an acyl-lysine.

The microorganisms described above were deposited under the terms of the Budapest Treaty on Jan. 24, 1991 in the Fermentation Research Institute in Japan.

Various other objects and advantages of the present invention will become obvious from the following description of the invention.

DETAILED DESCRIPTION OF THE PREFERRED EMBODIMENTS

The present invention relates to an improved process for L-lysine production and enhanced fermentation yields of L-lysine in microorganisms belonging to the genus Brevibacterium or Corynebacterium or mutants thereof. Applicants provide herein L-lysine-producing microorganisms or mutants thereof which have acquired resistance to either acyl-lysine or methylated acyl-lysine or a combination of both resistances that are suitable for use in the present invention.

In one embodiment, the present invention relates to a process for producing L-lysine by fermentation which comprises culturing a microorganism having a resistance to acyl-lysine or methylated acyl-lysine, or a combination of both resistances that is also capable of producing L-lysine, followed by collecting the produced and accumulated L-lysine in the culture broth. The microorganisms belong to the genus Brevibacterium or Corynebacterium.

The acyl-lysine used in the present invention refers to compounds containing a fatty acid residue having 5 to 20 carbon atoms bound to the amino group at the α-position or the ε-position or both the α- and ε- position of L- or DL-lysine through an acyl bond. Examples of such compounds include $N^\alpha$-stearoyl-L-lysine, $N^\epsilon$-decanoyl-L-lysine, $N^\epsilon$-myristoyl-L-lysine, $N^\epsilon$-palmitoyl-L-lysine, $N^\alpha$, $N^\epsilon$-octanolyl-L-lysine, and $N^\alpha$, $N^\epsilon$-dilauroyl-L-lysine.

The methylated acyl-lysine used in the present invention refers to acyl-lysine which is methylated at the amino group of the α-position. Examples of such compounds include $N^\alpha$-methyl-$N^\epsilon$-stearoyl-L-lysine, $N^\alpha$, $N^\alpha$-dimethyl-$N^\epsilon$-decanoyl-DL-lysine, $N^\alpha$, $N^\alpha$-dimethyl-$N^\epsilon$-palmitoyl-DL-lysine, $N^\alpha$, $N^\alpha$, $N^\alpha$-trimethyl-$N^\alpha$-myristoyl-DL-lysine and $N^\alpha$,$N^\alpha$,$N^\alpha$-trimethyl-$N^\epsilon$-palmitoyl-DL-lysine.

The mutants used in the present invention belong to the genus consisting of Brevibacterium and Corynebacterium, and have a resistance to an acyl-lysine, a methylated acyl-lysine or both an acyl-lysine and a methylated acyl-lysine. That is to say, the mutants may grow well in the presence of acyl-lysine even in a concentration of 25 mg/l or in the presence of methylated acyl-lysine even in a concentration of 25 mg/l or in the presence of both acyl-lysine and methylated acyl-lysine at a concentration of 25 mg/l each. These microorganisms have the further properties known to be necessary for acquiring the L-lysine productivity such as, for example, homoserine auxotrophy, S-(2-aminoethyl)-L-cysteine resistance, α-chlorocaprolactam resistance, or a combination thereof. By stating that the microorganism contains the property of growing well in the presence of acyl-lysine or methylated acyl-lysine means herein that the relative growth degree is at least 50 when the growth is set at 100 in the absence of the acyl-lysine and methylated acyl-lysine (measurements are in terms of turbitity when measured at 562 nm).

Specific examples of the mutants include:
Brevibacterium lactofermentum AJ 12592 (FERM BP-3239)
Brevibacterium lactofermentum AJ 12593 (FERM BP-3240)
Corynebacterium glutamicum AJ 12596 (FERM BP-3242)

The strains described above were deposited under the Budapest Treaty on Jan. 24, 1991 in the Fermentation Research Institute, Ministry of International Trade and Industry (FRI) located at 1-3, Hitgashi 1-chome, Tsukuba-shi, Ibaraki-ken, 305, Japan.

Microorganisms belonging to the genus Brevibacterium or Corynebacterium which are already known to produce L-lysine are used as the parent strains to obtain these mutants. In addition, wild strains of the genus Brevibacterium or Corynebacterium shown below may be used as the parent strains.
Brevibacterium lactofermentum ATCC 13869
Brevibacterium flavum ATCC 14067
Brevibacterium divaricatum ATCC 14020
Corynebacterium glutamicmm ATCC 13032
Corynebacterium acetoacidoohilum ATCC 13870
Corynebacterium acetoolutamicum ATCC 15806

After selecting for L-lysine productivity in these wild strains, resistance to the acyl-lysine and/or methylated acyl-lysine may also be selected. Alternatively, the resistance to the acyl-lysine and/or methylated acyl-lysine may be previously selected in these wild strains followed by selection of L-lysine productivity.

Conventional methods may be used for subjecting these parent strains to a mutation treatment, such as contacting with N-methyl-N'-nitro-N-nitrosoguanidine (hereinafter abbreviated as NG), for example. In order to screen the acyl-lysine and/or methylated acyl-lysine-resistant strains in these mutants, a method may be used which comprises collecting mutants which grow well in a medium containing a concentration of the acyl-lysine or methylated acyl-lysine that markedly inhibits growth of the parent strains. A more specific example of collecting the resistant strains is shown below.

Viable cells of Brevibacterium lactofermentum AJ 12435 FERM BP-2294) which is a L-lysine-producing microorganism having a resistance to S-(2-aminoethyl-L-cysteine) was treated with 250 μg/ml of NG at 30° C. for 30 minutes. The cells showing the survival rate of 1.0% were inoculated on an agar plate medium which is the minimum medium shown in Table 1 supplemented with 50 mg/l of $N^{\alpha},N^{\epsilon}N$-dioctanoyl-L-lysine which is an acyl-lysine. After culturing at 30° C. for a week, the grown colony was collected. The concentration of the acyl-lysine or methylated acyl-lysine supplemented to the medium is appropriately chosen depending on the minimum growth inhibitory concentration of the parent strain used and set to efficiently collect the desired resistant strains. One of the resistant strains isolated is Brevibacterium lactofermentum AJ 12592 (FERM BP-3239) which Was further provided for in the following example. Likewise, Brevibacterium lactofermentum AJ 12593 (FERM BP-3240) was obtained as an $N^{\alpha}$, $N^{\alpha}$, $N^{\alpha}$-trimethyl-$N^{\epsilon}$-palmitoyl-DL-lysine-resistant strain.

TABLE 1

| Component | Concentration |
| --- | --- |
| Glucose | 20 g/l |
| Ammonium sulfate | 10 g/l |
| KH$_2$PO$_4$ | 1 g/l |
| MgSO$_4$.7H$_2$O | 0.4 g/l |
| FeSO$_4$.7H$_2$O | 10 mg/l |
| MnSO$_4$.4H$_2$O | 10 mg/l |
| Biotin | 50 μg/l |
| Thiamine hydrochloride | 100 μg/l |
| Urea | 2 g/l |
| Agar | 20 g/l |

Further using Corynebacterium glutamicum AJ 3463 (FERM P-1987) as the parent strain, Corynebacterium glutamicum AJ 12596 (FERM BP-3242) was obtained as a $N^{\alpha}$, $N^{\alpha}$, $N^{\alpha}$-trimethyl-$N^{\epsilon}$-palmitoyl-DL-lysine-resistant strain.

Each of the isolated strains resistant to the acyl-lysine or methylated acyl-lysine was determined as indicated below and compared with that of the parent strain. The acyl-lysine or methylated acyl-lysine was added to the medium shown in Table 2 in each concentration and 4 ml of the medium was separately charged in a small test tube.

TABLE 2

| Component | Concentration |
| --- | --- |
| Sucrose | 20 g/l |
| Ammonium sulfate | 5 g/l |
| KH$_2$PO$_4$ | 1 g/l |
| MgSO$_4$.7H$_2$O | 0.4 g/l |
| FeSO$_4$.7H$_2$O | 10 mg/l |
| MnSO$_4$.4H$_2$O | 10 mg/l |
| Biotin | 100 μg/l |
| Thiamine hydrochloride | 200 μg/l |
| Nicotinamide | 5 mg/l |
| Protein hydrolysate | 1 g/l (calculated as nitrogen) |
| Urea | 3 g/l |

After sterilization, the test strain was inoculated on the medium. After shanking the culture at 30° C. for 24 hours, turbidity was measured at a wavelength of 562 nm and a relative growth rate was calculated based on the relative growth rate in the medium in which neither acyl-lysine nor methylated acyl-lysine was added. The results are shown in Table 3.

TABLE 3

| Strain Tested | Chemical | Concentration of Chemical | Relative Growth Rate |
| --- | --- | --- | --- |
| Brevibacterium lactofermentum AJ 12435 | $N^{\alpha},N^{\epsilon}$-dioctanoyl-L-lysine | 0 mg/l | 100 |
| | | 10 | 29 |
| | | 25 | 8 |
| | | 50 | 6 |
| | | 100 | 5 |
| Brevibacterium lactofermentum AJ 12592 | $N^{\alpha},N^{\epsilon}$-dioctanoyl-L-lysine | 0 mg/l | 100 |
| | | 10 | 92 |
| | | 25 | 81 |
| | | 50 | 14 |
| | | 100 | 10 |
| Brevibacterium | $N^{\alpha},N^{\alpha},N^{\alpha}$-trimethyl- | 0 mg/l | 100 |

TABLE 3-continued

| Strain Tested | Chemical | Concentration of Chemical | Relative Growth Rate |
|---|---|---|---|
| lactofermentum AJ 12435 | $N^\epsilon$-palmitoyl-DL-lysine | 10 | 48 |
| | | 25 | 9 |
| | | 50 | 8 |
| | | 100 | 5 |
| Brevibacterium lactofermentum AJ 12593 | $N^\alpha,N^\alpha,N^\alpha$-trimethyl-$N^\epsilon$-palmitoyl-DL-lysine | 0 mg/l | 100 |
| | | 10 | 100 |
| | | 25 | 53 |
| | | 50 | 13 |
| | | 100 | 11 |
| Corynebacterium glutamicum AJ 3463 | $N^\alpha,N^\epsilon$-dioctanoyl-L-lysine | 0 mg/l | 100 |
| | | 10 | 38 |
| | | 25 | 7 |
| | | 50 | 6 |
| | | 100 | 5 |
| Corynebacterium glutamicum AJ 12596 | $N^\alpha,N^\epsilon$-dioctanoyl-L-lysine | 0 mg/l | 100 |
| | | 10 | 100 |
| | | 25 | 93 |
| | | 50 | 45 |
| | | 100 | 24 |

The mutants of the present invention show a relative growth rate as good or better than 50 in the presence of acyl-lysine or methylated acyl-lysine in a concentration of 25 mg/l whereas the parent strains show a very poor relative growth rate of less than 10. As stated above, the mutants of the present invention are clearly distinguished over the parent strains since the mutants are resistant to the acyl-lysine or methylated acyl-lysine.

Using these resistant strains, L-lysine may be produced by fermentation in an ordinary nutrient medium containing carbon sources, nitrogen sources, inorganic ions, growth factors and nutrients required by the microorganism that are used in a conventional manner. The carbon sources that may be used are, for example, sugars such as glucose, sucrose, molasses or starch hydrolysates; organic acids such as acetic acid or propionic acid, and alcohols such as ethanol or propanol. The nitrogen sources that may be used are, for example, ammonium, sulfate, ammonium nitrate, ammonium chloride, urea or ammonia.

As conditions for culturing the strains, aerial culture is performed at a fermentation temperature of 24° to 37° C., preferably 30° to 34° C. The number of days required for the fermentation is generally 2 to 7 days. The pH at the beginning or during the fermentation is in the range of 5.0 to 8.5, preferably 6.0 to 7.5. For adjusting pH, inorganic or organic acidic or alkaline substances and further urea, calcium carbonate, ammonia gas or the like may be used.

After fermentation is completed, L-lysine is collected from the culture broth by known methods using an ion-exchange resin or crystallization, for example, or in combination thereof.

The following examples are given to further illustrate the present invention without being deemed limitative thereof.

EXAMPLES

Example 1

A medium containing 36 g/l of glucose, 20 g/l of ammonium chloride, 1 g/l of $KH_2PO_4$, 400 mg/l of $MgSO_4 \cdot 7H_2O$, 10 mg/l of $FeSO_4 \cdot 7H_2O$, 8 mg/l of $MnSO_4 \cdot 4H_2O$, 3 mg/l of soybean protein hydrolysate (calculated as nitrogen), 0.1 mg/l of thiamine hydrochloride and 0.3 mg/l of biotin (pH 7.0) was separately charged in volumes of 20 ml each in a shake flask of a 500 ml volume. After sterilization with heating at 115° C. for 10 minutes, 1 g of previously dry heat sterilized calcium carbonate was added to the flask. Each strain was inoculated on the medium followed by culturing at 31.5° C. for 48 hours while shaking. The amount of L-lysine accumulated in the culture broth was quantitatively determined by the acid-copper ninhydrin colorimetry. The results are shown in Table 4. In any of the resistant strains, accumulation of L-lysine was markedly increased as compared to the corresponding parent strain.

TABLE 4

| Strain | L-Lysine accumulated (g/l) | Yield Based on Sugar (%) |
|---|---|---|
| B. lactofermentum AJ 12435 (parent strain) | 9.5 | 26.4 |
| B. lactofermentum AJ 12592 (resistant strain) | 11.8 | 32.8 |
| C. glutamicum AJ 3463 (parent strain) | 7.0 | 19.5 |
| C. glutamicum AJ 12596 (resistant strain) | 10.7 | 29.7 |

Example 2

A medium having a composition of 80 g/l of blackstrap molasses when calculated as sugar, 50 g/l of ammonium sulfate, 1 g/l of $KH_2PO_4$, 1 g/l of $MgSO_4 \cdot 7H_2O$, 10 mg/l of soybean hydrolysate (calculated as nitrogen), 0.1 mg/l of thiamine hydrochloride and 0.3 mg/l of biotin (pH 7.0) was separately charged in a shake flask of 500 ml volume in a volume of 20 ml each. After sterilization with heating at 120° C. for 10 minutes, 1 g of calcium carbonate which had been previously sterilized by dry heating at 180° C. for 2 hours as added to the flask. Each strain was inoculated on the medium followed by culturing at 31.5° C. for 72 hours while shaking. The amount of L-lysine accumulated in the fermentation broth was assayed. The results are shown in Table 5. In the resistant strain, accumulation of L-lysine was markedly increased as compared to the parent strain.

TABLE 5

| Strain | L-Lysine accumulated (g/l) | Yield Based on Sugar % |
|---|---|---|
| B. lactofermentum AJ 12435 (parent strain) | 20.4 | 25.5 |

TABLE 5-continued

| Strain | L-Lysine accumulated (g/l) | Yield Based on Sugar % |
|---|---|---|
| B. lactofermentum AJ 12593 (resistant strain) | 24.8 | 31.0 |

While the foregoing invention has been described in some detail for purposes of clarity and understanding, it will be appreciated by one skilled in the art from a reading of this disclosure that various changes in form and detail can be made without departing from the scope of the invention.

What is claimed is:

1. A process for producing L-lysine, comprising culturing a L-lysine producing microorganism belonging to *Corynebacterium glutamicum* or in a *Brevibacterium lactofermentum* nutrient medium containing assimilable sources of carbon, nitrogen, and inorganic salts until a sufficient amount of L-lysine is produced and recovering said L-lysine, wherein said L-lysine producing microorganism exhibits a relative growth rate of at least 50 in the presence of 25 mg/l of a compound selected from the group consisting of acyl-lysine, methylated acyl-lysine, and mixtures thereof, based on a growth rate of 100 in the absence of said compound.

2. The process according to claim 1, wherein said microorganism is *Brevibacterium lactofermentum* AJ 12592 (FERM BP-3239).

3. The process according to claim 1, wherein said microorganism is *Brevibacterium lactofermentum* AJ 12593 (FERM BP-3240).

4. The process according to claim 1, wherein said microorganism is *Corynebacterium glutamicum* AJ 12596 (FERM BP-3242).

* * * * *

UNITED STATES PATENT AND TRADEMARK OFFICE
CERTIFICATE OF CORRECTION

PATENT NO. : 5,304,476
DATED : April 19, 1994
INVENTOR(S) : MANABU YOKOMORI ET AL It is certified that error appears in the above-identified patent and that said Letters Patent is hereby corrected as shown below:

Col.  Line 3,    27,    delete "acetoacidoohilum" and insert --acetoglutamicum--

3,    28,    delete "acetoolutamicum" and insert --acetoacidophilum--;

3,    53,    delete "$N^\alpha,N^\epsilon N$" and insert --$N^\alpha, N^\epsilon$--;

7,    17-18, delete "in a" before "Brevibacterium" and insert --in a-- after "Brevibacterium";

Signed and Sealed this

Twentieth Day of June, 1995

*Attest:*

BRUCE LEHMAN

*Attesting Officer*     *Commissioner of Patents and Trademarks*